United States Patent [19]
Houlihan et al.

[11] 3,944,570
[45] Mar. 16, 1976

[54] 3,3-DISUBSTITUTED PHTHALIDES

[75] Inventors: William J. Houlihan, Mountain Lakes; Jeffrey Nadelson, Lake Parsippany, both of N.J.

[73] Assignee: Sandoz, Inc., E. Hanover, N.J.

[22] Filed: June 27, 1974

[21] Appl. No.: 483,578

Related U.S. Application Data

[60] Division of Ser. No. 298,601, Oct. 18, 1972, Pat. No. 3,838,174, which is a continuation-in-part of Ser. No. 224,603, Feb. 8, 1972, abandoned.

[52] U.S. Cl. ... 260/343.4; 260/243 B; 260/247.2 B; 260/268 BC; 260/293.58; 260/326.34
[51] Int. Cl.² ........................................ C07D 493/00
[58] Field of Search ... 260/243 B, 247.2 B, 268 BC, 260/293.58, 326.3, 343.4

[56] References Cited
UNITED STATES PATENTS 3,301,870   1/1967   Terzijka et al. .................. 263/326.3

*Primary Examiner*—James A. Patten
*Attorney, Agent, or Firm*—Gerald D. Sharkin; Robert S. Honor

[57] ABSTRACT

Phthalanols disubstituted in the 3-position, e.g. 3-(4-chlorophenyl)-3-(2-dimethylaminomethyl phenyl)-1-methyl-1-phthalanol, prepared by alkylating corresponding phthalides, are useful as anti-inflammatory agents.

2 Claims, No Drawings

3,944,570

3,3-DISUBSTITUTED PHTHALIDES

This is a division of application Ser. No. 298,601 filed Oct. 18, 1972, now U.S. Pat. No. 3,838,174, which is a continuation-in-part of copending application Ser. No. 224,603, filed Feb. 8, 1972, now abandoned.

This invention pertains to 3,3-disubstituted phthalanols. More particularly, it concerns 1-alkyl-3,3-phenyl and substitutedphenyl-1-phthalanols, intermediates and acid addition salts thereof, and processes for their preparation.

The phthalanols of this invention may be represented by the following structural formula:

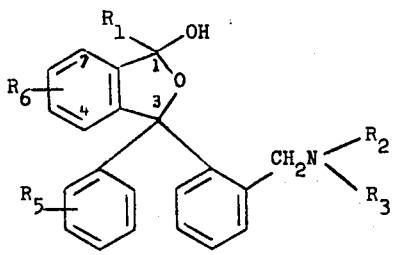

(I)

where
$R_1$, $R_2$ and $R_3$, each, independently, represent lower alkyl, i.e. alkyl of 1–4 carbon atoms, e.g. methyl, ethyl, propyl, isopropyl, butyl, and the like, or
$R_2$ and $R_3$ together represent $(CH_2)_x$
where $x$ is 4, 5, 6 or 7,

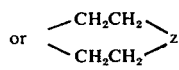

where $z$ represens O, S, or N—$R_4$
where $R_4$ represents lower alkyl as defined above, and
$R_5$ and $R_6$ each, independently, represent hydrogen, halo of atomic weight 19–36, trifluoromethyl, lower alkyl, as defined above, and lower alkoxy, i.e. alkoxy having 1–4 carbon atoms, such as methoxy, ethoxy, isopropoxy, and the like,
provided that $R_6$ may not represent halo at the 6-position, or lower alkyl at the 7-position.

The compounds of formula (I) are prepared from corresponding compounds of formula (II) according to the following reaction scheme:

where $R_2$, $R_3$, $R_5$ and $R_6$ and the provisos are as previously defined.

Compounds (II) may be converted into compounds (I) by treating the former in inert solvents with a compound of the formula $$R_1M \qquad (III)$$

where
$R_1$ is as defined above, and
M represents Li or MgX,
where X is halo having an atomic weight of about 35 to 102, followed by conventional hydrolysis, e.g. with water, saturated ammonium chloride solution, and the like. Solvents which may be used include ethyl ether, tetrahydrofuran and the like, or hydrocarbons such as benzene, toluene, pentane and the like. The reaction temperature is desirably about −10°C to +10°C, preferably about 0°C and the reaction may be carried out for about 1-5 hours. The particular time, temperature of reaction, and solvent used is not critica. The critical. may be carried out under the same conditions as the organo-metallic addition.

Compounds (II) represent a still further aspect of this invention and may be prepared according to the following reaction scheme:

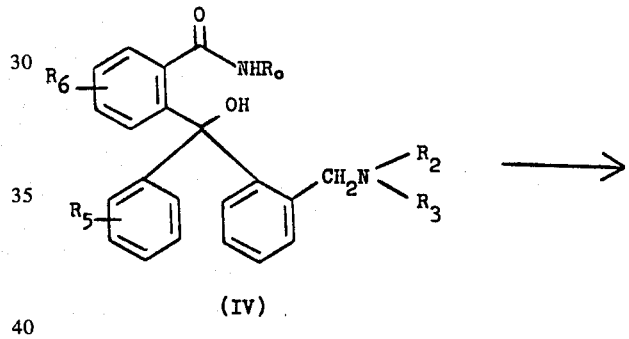

(IV)

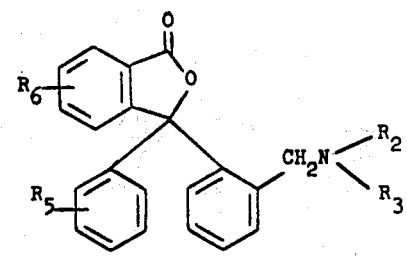

(II)

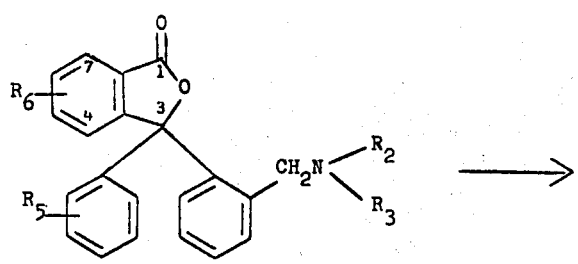

(II)

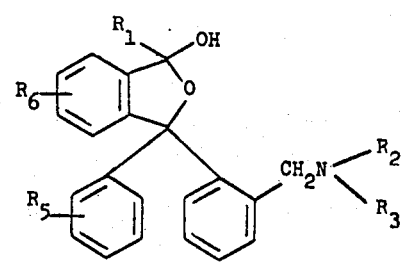

(I)

where $R_2$, $R_3$, $R_5$ and $R_6$ are as set out above, as are the provisos respecting compounds (II), provided also that respecting compounds (IV), $R_6$ may not represent halo at a position meta to the amido moiety or lower alkyl at a position ortho to the amido moiety, and $R_o$ represents lower alkyl, as defined above, or phenyl.

According to the above process, compound (IV) is heated in inert hydrocarbon or halogenated hydrocarbon solvent, e.g. benzene, toluene, pentane, o-dichlorobenzene and the like. The reaction may be carried out at a temperature of about 80°–200°C., and conveniently at the reflux temperature of the solvent utilized. The temperature and solvent are not critical in obtaining compounds (II).

The compounds of formula (IV) are novel and are obtainable according to the following reaction scheme:

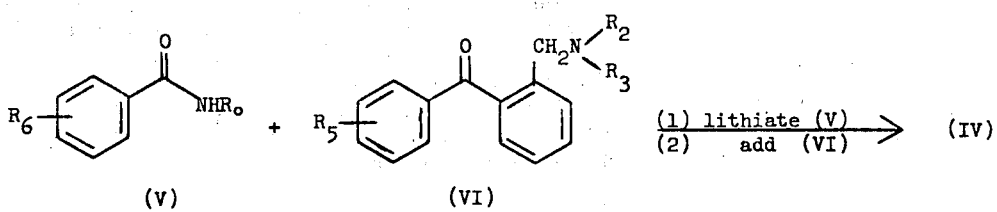

where $R_o$, $R_2$, $R_3$, $R_5$ and $R_6$ are as set out above as are the provisos respecting compounds (IV), provided also that respecting compounds (V), $R_6$ may not represent halo at a position meta to the amido moiety or lower alkyl at a position ortho to the amido moiety.

Compounds (IV) are prepared by first lithiating compounds (V), e.g. by use of a lower alkyl or aryl lithium compound, such as n-butyl lithium, in inert hydrocarbon or ether solvent, e.g. benzene, toluene, ethyl ether, tetrahydrofuran and the like to obtain a dilithio intermediate thereof, which in turn is normally not recovered but is treated with a benzophenone (VI) to obtain compounds (IV). The lithiation is preferably performed at a temperature between about −60° to +10°C. for about 1–3 hours. The temperature and solvent used are not critical.

Unless indicated otherwise, the products of each of the reactions described above are recovered by conventional techniques such as crystalization, filtration, trituration, and the like.

Certain of the compounds of formulas (III), (V) and (VI) are known and may be prepared according to methods disclosed in the literature. The compound of formula (III), (V) and (VI) not specifically disclosed may be prepared by methods analogous to those in the literature from known compounds.

It will be understood that certain of the compounds of formulas (I), (II), and (IV) exist in racemic form or in the form of optically active isomers. The separation and recovery of the respective isomers may be readily accomplished employing conventional techniques and such isomers are included within the scope of the invention.

Compounds (I), (II), (IV) and (VI) may exist in the form of their acid addition salts. Said salts and their respective free bases may be converted from one to the other by conventional techniques and are chemically interchangeable for purposes of the above described processes.

The compounds of formula (I) above are useful because they possess pharmacological properties in animals, such as mammals. In particular, the compounds may be used as anti-inflammatory agents as indicated by their activity in rats orally administered active agent at a dose of 10–100 mg/kg of animal body weight. Edema is induced by carrogeenan and the rats are treated according to the method of Winter (Proc. Soc. Exp. Biol., 111:544, 1962).

For such usage, the compounds of formula (I) may be combined with a pharmaceutically acceptable carrier or adjuvant, and may be administered orally in such forms as tablets, capsules, elixers, suspensions and the like, or parenterally in the form of an injectable solution or suspension. The dosage will vary depending upon the mode of administration utilized and the particular compounds employed.

As indicated above, the compounds of formula (I) may be similarly administered in the form of their nontoxic pharmaceutically acceptable acid addition salts. Such salts possess the same order of activity as the free base, are readily prepared by reacting the base with an appropriate acid and accordingly are included within the scope of the invention. Representative of such salts are the mineral salts, such as hydrochloride, hydrobromide, sulfate, phosphate and the like and the organic acid salts, such as the succinate, benzoate, acetate, p-toluensulfonate, benzensulfonate and the like.

As noted avove, the compounds of formula (I) exist as optical isomers. In some cases greater pharmacological activity or other beneficial attribute may be found for a particular isomer and in such instances administration of such isomer may be preferred.

In general, satisfactory results are obtained when the compounds (I) are administered orally at a daily dosage of from about 1–200 mg/kg of animal body weight, preferably given in divided doses, 2 to 4 times a day or in sustained release form. For most larger mammals (e.g., primates) the total daily dosage is from about 75–1000 mg per day. Dosage forms suitable for internal use comprises from about 20 to about 500 mg of the active compound in intimate admixture with a solid or liquid pharmaceutically acceptable carrier of diluent.

Tablets and capsules containing the ingredients indicated below may be prepared by conventional techniques and are useful in treating inflammation at a dose of one tablet or capsule 2 to 4 times a day.

| Ingredients | Weight (mg.) | |
|---|---|---|
| | Tablet | capsule |
| 3-(4-chlorophenyl)-3-(2-dimethylaminomethyl phenyl)-1-methyl-1-phthalanol | 50 | 50 |
| tragacanth | 10 | — |
| lactose | 197.5 | 250 |
| corn starch | 25 | — |
| talcum | 15 | — |
| magnesium stearate | 2.5 | — |
| Total | 300.0 mg. | 300.0 mg. |

The following pharmaceutical compositions are formulated with the indicated amount of active agent using conventional techniques. The injectable solution and the oral liquid solution represent formulations useful in the treatment of inflammation:

| | Injectable Weight % | Liquid Weight % |
|---|---|---|
| 3-(4-chlorophenyl)-3-(2-dimethylaminomethyl phenyl)-1-methyl-1-phthalanol | 10 | 0.5 to 3.5 |
| sodium alginate | 0.5 | — |
| sodium benzoate | — | 0.1 to 0.5 |
| simple syrup | — | 30 to 70 |
| lecithin | 0.5 | — |
| sodium chloride | as desired | — |
| flavor | — | as desired |
| color | — | as desired |
| sorbitol solution 70% USP | — | 10 to 30 |
| buffer agent to adjust pH for desired stability | as desired | as desired |
| water | to desired volume | to desired volume |

EXAMPLE 3-(4-chlorophenyl)-3-(2-dimethylaminomethyl phenyl)-1-methyl-1-phthalanol Steps 1 and 2:
α-(4-chlorophenyl)-α-(2-dimethylaminomethyl phenyl)-α-hydroxy-N-methyl-o-toluamide To a flask equipped with a stirrer, dropping funnel, condenser and gas inlet tube maintained under a nitrogen atmosphere there is added at room temperature 19.7 g (0.146 mole) of N-methyl benzamide and 400 ml. dry tetrahydrofuran. The reaction flask is immersed in an ice bath and cooled to an internal temperature of 5°C. Stirring is initiated and 204 ml. of 1.6 M. n-butyl lithium (~0.321 mole) in hexane is added dropwise over about 1 hour maintaining the temperature below 8°C. The resulting dilithio salt is stirred at 5°C. for an additional hour and then a solution of 40 g. (0.146 mole) of 4'-chloro-2-dimethylaminomethyl benzophenone in 500 ml. tetrahydrofuran is added dropwise over about 1 hour maintaining the temperature between −10 to 10°C. The resulting mixture is stirred at 5°C. for 1 hour longer and 150 ml. of saturated ammonium chloride is added maintaining the temperature at about 10°C. The layers are separated and the organic phase dried over ahydrous magnesium sulfate, filtered and evaporated in vacuo. The residue is crystallized from ether to give α-(4-chlorophenyl)-α-(2-dimethylaminomethyl phenyl)-α-hydroxy-N-methyl-o-toluamide; m.p. 154°–156°C.

When the above process is carried out and in place of N-methyl benzamide there is used
a. o-chloro-N-phenyl benzamide,
b. N-methyl-p-toluamide,
c. N-methyl-m-trifluoromethyl benzamide,
d. o-ethoxy-N-methylbenzamide,
e. p-chloro-N-methylbenzamide, or
f. p-methoxy-N-methylbenzamide,
there is obtained a. 3-chloro-α-(4-chlorophenyl)-α-(2-dimethylaminomethyl phenyl)-α-hydroxy-N-phenyl-2-toluamide,
b. α-(4-chlorophenyl)-α-(2-dimethylaminomethyl phenyl)-4,N-dimethyl α-hydroxy-2-toluamide,
c. α-(4-chlorophenyl)-α-(2-dimethylaminomethyl phenyl)-α-hydroxy-N-methyl-4-trifluoromethyl-2-toluamide,
d. α-(4-chlorophenyl)-α-(dimethylaminomethyl phenyl)-3-ethoxy-α-hydroxy-N-methyl-2-toluamide,
e. α-(4-chlorophenyl)-α-(2-dimethylaminomethyl phenyl)-4-chloro-α-hydroxy-N-methyl-2-toluamide, or
f. α-(4-chlorophenyl)-α-(2-dimethylaminomethyl phenyl)-4-methoxy-α-hydroxy-N-methyl-2-toluamide, respectively.

When the above process is carried out and in place of 4'-chloro-2-dimethylaminomethyl benzophenone there is used
g. 2-dimethylaminomethyl benzophenone,
h. 2'-methoxy-2-piperidinomethyl benzophenone,
i. 2-morpholinomethyl-3'-trifluoromethyl benzophenone,
j. 4'-ethyl-2-thiomorpholinomethyl benzophenone,
k. 2-(N-methylpiperazinomethyl)-benzophenone,
l. 2-dimethylaminoethyl-4'-methylbenzophenone, or
m. 2-morpholinomethyl benzophenone,
there is obtained
g. α-(2-diethylaminomethyl phenyl)-α-hydroxy-N-methyl-α-phenyl-o-toluamide,
h. α-hydroxy-α-(2-methoxyphenyl)-N-methyl-α-(2-piperidinomethyl phenyl)-o-toluamide,
i. α-hydroxy-N-methyl-α-(2-morpholinomethyl phenyl)-α-(3-trifluoromethylphenyl)-o-toluamide, j. α-hydroxy-α-(4-ethylphenyl)-N-methyl-α-(2-thiomorpholinomethyl phenyl)-o-toluamide,
k. α-hydroxy-N-methyl-α-[2-(N-methylpiperazinomethyl)phenyl]-α-phenyl-o-toluamide,
l. α-(4-methylphenyl)-α-(2-dimethylaminomethyl phenyl)-α-hydroxy-N-methyl-o-toluamide, or
m. α-hydroxy-N-methyl-α-[2-(morpholinomethyl phenyl] α-phenyl-o-toluamide, respectively.

Step 3. 3-(4-chlorophenyl)-3-(2-dimethylaminomethyl phenyl) phthalide

A mixture of 40.8 g. (0.1 mole of α-(4-chlorophenyl)-α-(2-dimethylaminomethyl phenyl)-α-hydroxy-N-metyl-o-toluamide and 200 ml. o-dichlorobenzene is refluxed for 20 hours, cooled and the solvent is removed in vacuo. The residue is triturated with ether and the resulting solid is recrystallized from ether-methylene chloride (1:1) to give 3-(4-chlorophenyl)-3-(2-dimethylaminomethyl phenyl) phthalide; m.p. 138.5° – 140°C.

When the process of step 3 above is carried out and in place of α-(4-chlorophenyl)-α-(2-dimethylaminomethyl phenyl)-α-hydroxy-N-methyl-o-toluamide there is used
a. 3-chloro-α-(4-chlorophenyl-α-(2-dimethylaminomethyl phenyl)-α-hydroxy-N-phenyl-2-toluamide,
b. α-(4-chlorophenyl)-α-(2-dimethylaminomethyl phenyl)-5,N-dimethyl-α-hydroxy-2-toluamide,
c. α-(4-chlorophenyl)-α-(2-dimethylaminomethyl phenyl)-α-hydroxy-N-methyl-4-trifluoromethyl-2-toluamide,
d. α-(4-chlorophenyl)-α-(2-dimethylaminomethyl phenyl)-3-ethoxy-α-hydroxy-N-methyl-2-toluamide,
e. α-(4-chlorophenyl)-α-(2-dimethylaminomethyl phenyl)-4-chloro-α-hydroxy-N-methyl-o-toluamide,
f. α-(4-chlorophenyl)-α-(2-dimethylaminomethyl phenyl)-4-methoxy-α-hydroxy-N-methyl-2-toluamide,
g. α-(2-diethylaminomethyl phenyl)-α-hydroxy-N-methyl-α-phenyl-o-toluamide,
h. α-hydroxy-α-(2-methoxyphenyl)-N-methyl-α-(2-piperidinomethyl phenyl)-o-toluamide,
i. α-hydroxy-N-methyl-α-(2-morpholinomethyl phenyl)-α-(3-trifluoromethylphenyl)-o-toluamide,
j. α-hydroxy-α-(4-ethylphenyl)-N-methyl-α-(2thiomorpholinomethyl phenyl)-o-toluamide,
k. α-hydroxy-N-methyl-α-[2-(N-methylpiperazinomethyl)phenyl]-α-phenyl-o-toluamide,
l. α-(4-methylphenyl)-α-(2-dimethylaminomethyl phenyl)-α-hydroxy-N-methyl-o-toluamide, or
m. α-hydroxy-N-methyl-α-[2-(morpholinomethyl)-phenyl] α-phenyl-o-toluamide,
there is obtained
a. 7-chloro-3-(4-chlorophenyl)-3-(2-dimethylaminomethyl phenyl) phthalide,
b. 3-(4-chlorophenyl)-3-(2-dimethylaminomethyl phenyl)-5-methyl phthalide,
c. 3-(4-chlorophenyl)-3-(2-dimethylaminomethyl phenyl)-6-trifluoromethyl phthalide,
d. 3-(4-chlorophenyl)-3-(2-dimethylaminomethyl phenyl)-7-ethoxy phthalide,
e. 3-(4-chlorophenyl)-3-(2-dimethylaminomethyl phenyl)-5-chloro phthalide,
f. 3-(4-chlorophenyl)-3-(2-dimethylaminomethyl phenyl)-5-methoxy phthalide,
g. 3-(2-diethylaminomethyl phenyl)-3-phenyl phthalide,
h. 3-(2-methoxyphenyl)-3-(2-piperidinomethyl phenyl) phthalide,
i. 3-(2-morpholenomethyl phenyl)-3-(3-trifluoromethylphenyl) phthalide,
j. 3-(4-ethylphenyl)-3-(2-thiomorpholinomethyl phenyl) phthalide,
k. 3-[2-(N-methylpiperazinomethyl)phenyl]-3-phenyl phthalide,
l. 3-(4-methylphenyl)-3-(2-dimethylaminomethyl phenyl) phthalide, or
m. 3-[2-(morpholinomethyl)phenyl]-3-phenyl phthalide, respectively.

Step 4. 3-(4-chlorophenyl)-3-(2-dimethylaminomethyl phenyl)-1-methyl-1-phthalanol.

A solution of 9.8 g. 3-(4-chlorophenyl)-3-(2-dimethylaminomethyl phenyl) phthalide (0.026 mole) in 60 ml. of ether and 10 ml. of tetrahydrofuran is cooled to 0°C. and 26 ml. of 1.5 M. methyl lithium (0.039 mole) in 25 ml. of ether was added dropwise in about 0.5 hr. while maintaining the temperature at about 0°C. The resulting mixture is stirred for 2 hours at 0°C. and then treated with 50 ml. of water. The resulting solid is filtered, washed with ether and recrystallized from methylene chloride/methanol (1:1) to give 3-(4-chlorophenyl)-3-(2-dimethylaminomethyl phenyl)-1-methyl-1-phthalanol; m.p. 206.5° to 207°C.

When the process of step 4 above is carried out and in place of 3-(4-chlorophenyl)-3-(2-dimethylaminomethyl phenyl) phthalide, there is used
a. 7-chloro-3-(4-chlorophenyl)-3-(2-dimethylaminomethyl phenyl) phthalide,
b. 3-(4-chlorophenyl)-3-(2-dimethylaminomethyl phenyl)-5-methyl phthaide,
c. 3-(4-chlorophenyl)-3-(2-dimethylaminomethyl phenyl)-6-trifluoromethyl phthalide,
d. 3-(4-chlorophenyl)-3-(2-dimethylaminomethyl phenyl)-7-ethoxy phthalide,
e. 3-(4-chlorophenyl)-3-(2-dimethylaminomethyl phenyl)-5-chloro phthalide,
f. 3-(4-chlorophenyl)-3-(2-dimethylaminomethyl phenyl)-5-methoxy phthalide
g. 3-(2-diethylaminomethyl phenyl)-3-phenyl phthalide,
h. 3-(2-methoxyphenyl)-3-(2-piperidinomethyl phenyl) phthalide,
i. 3-(2-norpholenomethyl phenyl)-3-(3-trifluoromethylphenyl) phthalide,
j. 3-(4-ethylphenyl)-3-(2-thiomorpholinomethyl phenyl)phthalide,
k. 3-[2-N(methylpiperazinomethyl) phenyl]-3-phenyl phthalide,
l. 3-(4-methylphenyl)-3-(2-dimethylaminomethyl phenyl) phthalide, or
m. 3-[2-(morpholinomethyl)phenyl]-3-phenyl phthalide,
there is obtained
a. 7-chloro-3-(4-chlorophenyl)-3-(2-dimethylaminomethyl phenyl)-1-methyl-1-phthalanol,
b. 3-(4-chlorophenyl)-3-(2-dimethylaminomethyl phenyl)-1,5-dimethyl-1-phthalanol,
c. 3-(4-chlorophenyl)-3-(2-dimethylaminomethyl phenyl)-1-methyl-6-trifluoromethyl-1-phthalanol,
d. 3-(4-chlorophenyl)-3-(2-dimethylaminomethyl phenyl)-7-ethoxy-1-methyl-1-phthalanol, e. 3-(4-chlorophenyl)-3-(2-dimethylaminomethyl phenyl)-5-chloro-1-methyl-1-phthalanol,
f. 3-(4-clorophenyl)-3-(2-dimethylaminomethyl phenyl)-5-methoxy-1-methyl-1-phthalanol,
g. 3-(2-diethylaminomethyl phenyl)-1-methyl-3-phenyl-1-phthalanol,
h. 3-(2-methoxyphenyl)-1-methyl-3-(2-piperidinomethyl phenyl)-1-phthalanol,
i. 1-methyl-3-(2-morpholinomethyl phenyl)-3-(3-trifluoromethyl-phenyl)-1-phthalanol,
j. 3-(4-ethylphenyl)-1-methyl-3-(2-thiomorpholinomethyl phenyl)-1-phthalanol,
k. 1-methyl-3-[2-(N-methylpiperazinomethyl) phenyl]-3-phenyl-1-phthalanol,
l. 3-(4-methylphenyl)-3-(2-dimethylaminomethyl phenyl)-1-methyl-1-phthalanol, or
m. 1-methyl-3-[2-(morpholinomethyl phenyl]-3-phenyl-1-phthalanol, respectively.

When the above procedure of step 4 is carried out and in place of methyl lithium there is used n-propyl magnesium or n-ethyl lithium, the corresponding phthalanols indicated above but substituted at the 1-position with a n-propyl moiety or n-ethyl moiety respectively in place of a methyl group are obtained.

What is claimed is:
1. A compound of the formula

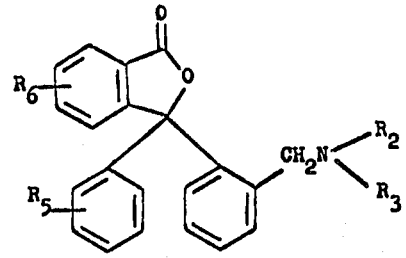

where
$R_2$ and $R_3$ each, independently, represent lower alkyl, or
$R_2$ and $R_3$ together represent $(CH_2)_x$
where $x$ represents 4, 5, 6 or 7,

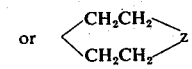

where $z$ represents O, S, or $N-R_4$
where
$R_4$ represents lower alkyl,
$R_5$ and $R_6$ each, independently, represent H, halo of atomic weight 19–36, lower alkyl, lower alkoxy or trifluorometyl,
provided that $R_6$ may not represent halo at the 6-position or lower alkyl at the 7-position,
or an acid addition salt thereof.

2. A compound according to claim 1 which is 3-(4-chlorophenyl)-3-(2-dimethylaminomethyl phenyl) phthalide.

* * * * *